(12) United States Patent
Buonoato

(10) Patent No.: US 7,511,173 B2
(45) Date of Patent: Mar. 31, 2009

(54) CREATINE SALT WITH ENHANCED NUTRITIONAL AND THERAPEUTIC EFFICACY AND COMPOSITIONS CONTAINING SAME

(75) Inventor: Antonietta Buononato, Rome (IT)

(73) Assignee: Iovate T & P Inc., Oakville, Ontario (CA)

( * ) Notice: Subject to any disclaimer, the term of this patent is extended or adjusted under 35 U.S.C. 154(b) by 294 days.

(21) Appl. No.: 11/569,557

(22) PCT Filed: Mar. 16, 2005

(86) PCT No.: PCT/IT2005/000145

§ 371 (c)(1),
(2), (4) Date: Nov. 22, 2006

(87) PCT Pub. No.: WO2005/089734

PCT Pub. Date: Sep. 29, 2005

(65) Prior Publication Data

US 2008/0234372 A1    Sep. 25, 2008

(30) Foreign Application Priority Data

Mar. 19, 2004   (IT)  .......... RM2004A0143

(51) Int. Cl.
*C07C 229/00*   (2006.01)
*A61K 47/00*   (2006.01)

(52) U.S. Cl. .................. 562/561; 424/439

(58) Field of Classification Search ........ 562/561; 424/439

See application file for complete search history.

(56) References Cited

FOREIGN PATENT DOCUMENTS

WO    WO 02/076931    10/2002

OTHER PUBLICATIONS

Elizabeth Hyde, Glycine and Histidine Feeding and Creatine . . . , Journal of Biological Chemistry, vol. 134, pp. 95-103, 1940, XP002389570.

*Primary Examiner*—Jafar Parsa

(57) ABSTRACT

The novel salt creatine glycinate and compositions (dietary supplements, energy drinks, and dietetic or pharmaceutical products containing the same are described.

8 Claims, No Drawings

CREATINE SALT WITH ENHANCED NUTRITIONAL AND THERAPEUTIC EFFICACY AND COMPOSITIONS CONTAINING SAME

The present invention relates to a novel stable and non-hygroscopic creatine salt with enhanced nutritional and/or therapeutic efficacy and to compositions that can be used as dietary supplements, energy drinks, dietetic products, nutraceuticals, health foods and drugs containing said creatine salt as active principle.

More particularly, this novel compound is the salt of creatine with glycine, which will be referred to hereinbelow as creatine glycinate.

In recent years, the use of dietary supplements, energy drinks nutraceuticals and health foods containing substances of natural origin as active principles has become more and more widespread, arousing the interest of increasingly broad classes of consumers.

Creatine is a natural product which, by virtue of its physiological activity, has aroused considerable interest among both the scientific community and consumers.

Creatine is a natural amino acid present in the heart, the retina, the brain, skeletal muscle and other organs. In skeletal muscle, about a quarter of the creatine present exists as free creatine, and three-quarters as phosphocreatine. Creatine is mainly synthesized in the liver, the kidneys and the pancreas, in amounts of 1-2 grams per day, and an additional amount (1-2 grams) is assimilated from the diet in fish and meat.

It is mainly excreted via the kidneys after having been irreversibly converted by skeletal muscle into creatinine. Both creatine and phosphocreatine play an important role in the anaerobic production of ATP during short and intensive exertions, via the creatine kinase system. Specifically, during muscle contraction, there is an increase in the amount of phosphocreatine (which is generated from creatine) and consequently in ATP; thus, supplementing the diet with creatine can increase the concentration of phosphocreatine in muscles by 6 to 16%, with a consequent increase in the ATP turnover during physical exertion. It should also be mentioned that a pharmaceutical specialty exists, Neoton, containing creatine phosphate, which is administered parenterally as a cardioprotective agent after surgery or to reduce cardiac insufficiency after episodes of ischemia. By virtue of these characteristics, creatine has met with enormous success among athletes in recent years as a dietary supplement.

Creatine is taken particularly by athletes and sportspeople in general since it increases muscle mass if its intake is accompanied by constant physical activity. This results in a reduction in the level of fat and an increase in muscle mass. Recent research has demonstrated that combining creatine with carbohydrates increases its effects due to the production of insulin, which is stimulated by simple sugars, which quite probably play a role in transporting creatine into muscle cells.

Glycine is abundant in milk and is not an essential amino acid. It is present in liver-detoxifying compounds such as glutathione (of which it is an essential component, together with cysteine and glutamic acid). Glycine is essential for the biosynthesis of nucleic acids and bile acids, and is therefore also directly involved in the endogenous synthesis of creatine. It is a glucogenic amino acid (i.e. a sugar-producing amino acid).

It is readily converted into serine, which is a basic component for a number of amino acid compounds used as tonic preparations.

In experiments conducted on human beings, it was found that glycine promotes the secretion of gastric acids and, as a result, is used in many gastric antacid agents. It is one of the most important amino acids as regards hair nutrition, and is the most abundant amino acid in collagen. It also has growth hormone-stimulating properties.

It has been found that the novel creatine glycinate salt having the formula

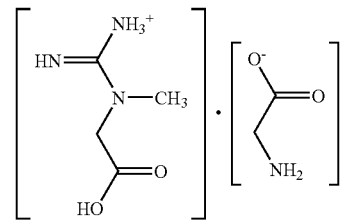

is a non-hygroscopic compound that is also stable in aqueous solution and that shows synergistic activity in the presence of creatine and glycine.

Glycine is of great value as a source of creatine, which is essential for muscle function; it releases energy by breaking down glycogen; it produces glucogen, which mobilizes glycogen (glucose-based energy reserve) from the liver; it improves the immune system; it acts as a nitrogen pool for the synthesis of the non-essential amino acids. In addition, its synergy with creatine gives the latter appreciable stability in aqueous solution.

Creatine monohydrate is the product widely used as dietary supplement, but has problems of solubility (17 mg/ml), stability and palatability, and therefore formulation problems. To improve this aspect, salts containing creatine have been introduced onto the market, for instance the citrate, which is preferred by the public since it is more palatable and more soluble (48 mg/ml of creatine), but it does not improve its stability in water. Specifically, when solutions with a concentration of about 15 mg/ml—1.5% (normally used by sportspeople) are prepared, the titer drops by about 50% after 10 days at room temperature. The mechanism of degradation is due to the release of creatine from the salt, which, on becoming converted into the monohydrate, partly precipitates, since it is sparingly soluble, and partly becomes converted into creatinine (a product which is toxic to the kidneys), the latter reaction being facilitated by the presence of citric acid. None of this occurs in the case of the novel creatine glycinate salt, which presents a range of advantages:

- it improves the solubility of creatine monohydrate (25 mg/ml)
- the presence, in addition, of glycine as the anionic part, gives this salt pleasant organoleptic properties (sweet taste) and no aftertaste
- its neutral pH also makes it stable in aqueous solution and, after 10 days, not the least sign of degradation into creatinine is observed.

The nonlimiting example that follows describes the preparation and the physicochemical characteristics of the compound according to the invention.

EXAMPLE

Creatine Glycinate 75 g (1 mol) of glycine were dissolved in 150 ml of water and the resulting suspension was maintained at 50° C. for about 30 minutes. 149 grams (2 mol) of creatine monohydrate were then added to the clear solution, and the resulting mixture was maintained at 50° C. for about 60 minutes.

By the end of this time period, the reaction mixture, which was initially fluid and smooth-flowing, became dense and soapy. The heating was then stopped.

500 ml of acetone were added to the reaction mixture, and the resulting mixture was kept stirring until its temperature had fallen spontaneously to room temperature. The reaction product was filtered off and the filter cake was dried.

220 grams of creatine glycinate (yield: 97%) were obtained in the form of a white crystalline solid.

| Physicochemical characteristics: | |
|---|---|
| Empirical formula: | $C_4H_{10}N_3O_2 \cdot C_2H_4NO_2$ |
| Molecular weight: | 206.19 |
| Composition: | 67% creatine-33% glycine |
| Appearance: | white crystalline powder |
| Odor: | odorless |
| Taste: | pleasant, slightly sweet |
| m.p.: | 232-33° C. by decomposition |
| pH: | 6; c = 1% in water |
| Solubility: | 1 g/35 ml of water at 25° C. |
| K.F.: | 5% |
| 1H NMR: | 3.8 (2H, s, $\underline{CH_2}$—COOH); 3.4 (2H, s, $NH_2$—$\underline{CH_2}$—COO—). |

The compositions according to the invention comprising creatine glycinate as active principle may also appropriately comprise, besides at least one of the usual pharmacologically acceptable excipients, the choice of which is within the scope of a person skilled in the art of pharmaceutical technology, other active principles, amino acids, antioxidants, mineral substances, vitamins, coenzymes and plant extracts.

Preferred examples of these other ingredients are, in a nonlimiting manner, α-lipoic acid (which has known antioxidant and toxic metal scavenging activity), L-carnitine and salts thereof, acetyl-L-carnitine and salts thereof, coenzyme Q10, the bioavailable forms of mineral substances such as selenium, magnesium and zinc, for instance selenomethionine, and plant extracts.

The compositions may be administered in the form of tablets, chewable tablets, capsules, sachets, granules, powders, syrup, drops and energy drinks. The compositions, in unit dosage form, comprise from about 250 to 1000 mg and preferably from about 250 to 500 mg of creatine glycinate.

The compositions are conveniently in the form of dietary supplements, dietetic products, nutraceuticals, energy drinks, health foods or medicinal products.

The invention claimed is:
1. Creatine glycinate of formula

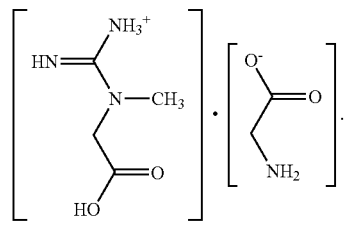

2. A composition comprising, as active principle, creatine glycinate and at least one pharmacologically acceptable excipient.

3. The composition as claimed in claim 2, comprising at least one further ingredient chosen from active principles, amino acids, antioxidants, mineral substances, vitamins and coenzymes.

4. The composition as claimed in claim 3, in which the further ingredient is chosen from the group comprising L-carnitine and salts thereof, acetyl-L-carnitine and salts thereof, α-lipoic acid, coenzyme $Q_{10}$ and bioavailable forms of selenium, magnesium and zinc, and plant extracts.

5. The composition of any of claim 2-4, in the form of tablets, chewable tablets, capsules, sachets, granules, powders, syrup or drops and energy drinks.

6. The composition of claim 2, in a unit dosage form comprising 250-1000 mg of creatine glycinate.

7. The composition of claim 2, for human use as a dietary supplement, a dietetic product, a nutraceutical, an energy drink, a health food or a medicinal product.

8. The composition of claim 2, in a unit dosage form comprising 250-500 mg of creatine glycinate.

\* \* \* \* \*